United States Patent [19]

Schoknecht et al.

[11] 4,116,040
[45] Sep. 26, 1978

[54] TISSUE SIMULATING CALIBRATION AND REFERENCE STANDARD

[76] Inventors: Günter Schoknecht, Mühlenstrasse 5, 1000 Berlin 37; Udo Flesch, Fontanestrasse 7, 1000 Berlin 33, both of Fed. Rep. of Germany

[21] Appl. No.: 852,092

[22] Filed: Nov. 16, 1977

[30] Foreign Application Priority Data

Nov. 22, 1976 [DE] Fed. Rep. of Germany ....... 2653384

[51] Int. Cl.² .............................................. G01C 25/00
[52] U.S. Cl. ...................................................... 73/1 R
[58] Field of Search ............. 73/1 R, 1 DV, 570, 574, 73/579, 627, 596

[56] References Cited

U.S. PATENT DOCUMENTS

| | | | |
|---|---|---|---|
| 3,924,444 | 12/1975 | Heyman et al. | 73/1 R |
| 3,933,026 | 1/1976 | Ham et al. | 73/1 R |
| 3,975,939 | 8/1976 | McLean | 73/1 DV |

*Primary Examiner*—Jerry W. Myracle
*Attorney, Agent, or Firm*—Smyth, Pavitt, Siegemund, Jones & Martella

[57] ABSTRACT

A standard to be used for calibrating ultrasonic equipment is comprised of plural, flat parallelly oriented containers alternately filled with castor oil and a mineral oil.

4 Claims, 1 Drawing Figure

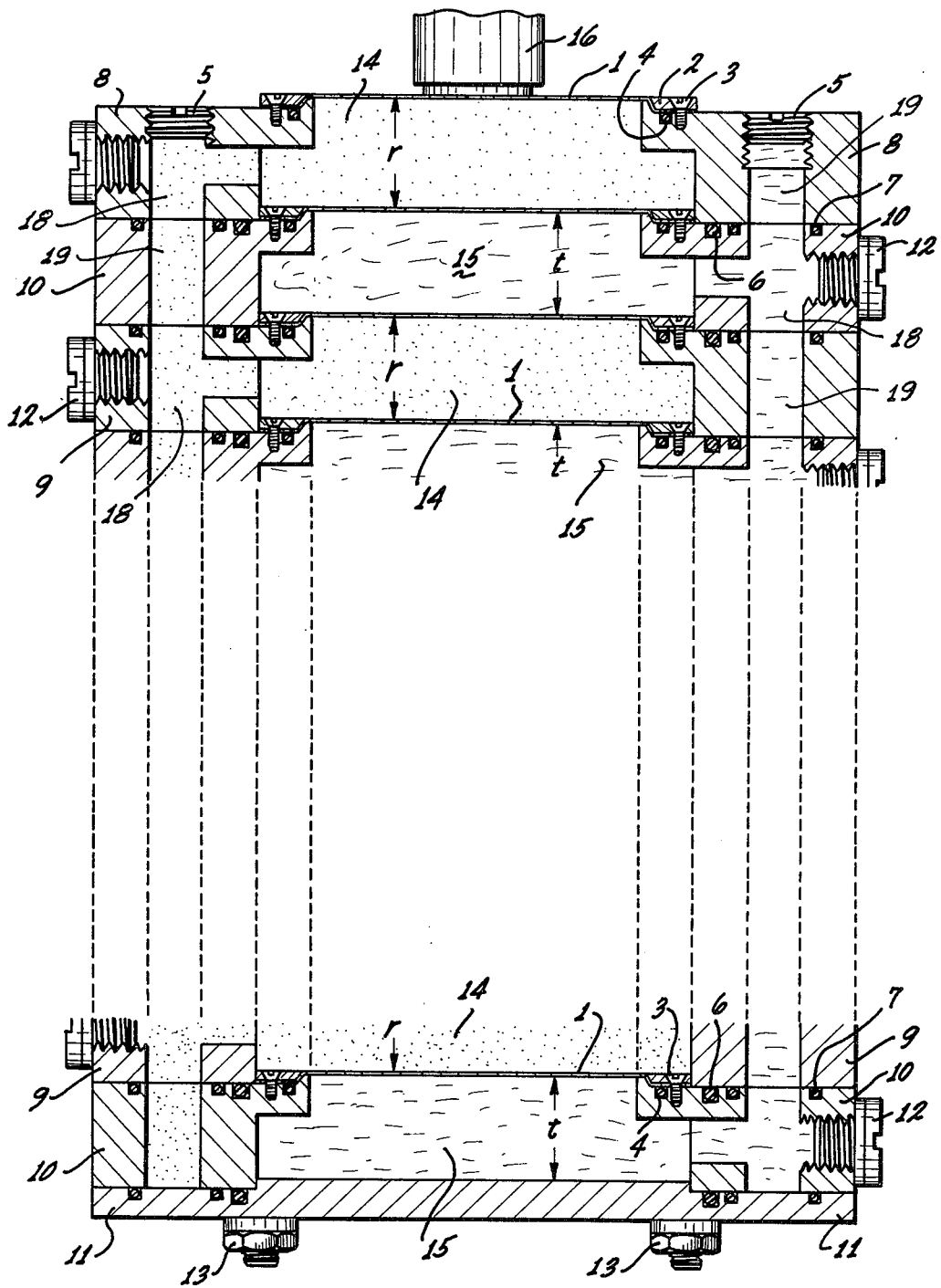

TISSUE SIMULATING CALIBRATION AND REFERENCE STANDARD

BACKGROUND OF THE INVENTION

The present invention relates to a calibration dummy or reference standard for simulating animal or human cell tissue, for purposes of calibrating, adjusting or, more generally, testing ultrasonic equipment.

It is known to employ ultrasonics for purposes of medical diagnostics. Particularly ultrasonic pulses are transmitted to the body and tissue boundaries produce reflection of these pulses. The transit time of such pulses permits the determination of the depth of such a boundary.

Generally speaking, the acoustic impedance of a material is the product of its density $p$ and of the speed $c$ of acoustic waves therein. Whenever a beam of acoustic waves such as ultrasonic waves passes through a boundary defined by a steep change in the acoustic impedance, a portion of the vibration energy is reflected, while the remainder passes through the boundary. The reflected signal portion or echo is detected and the transit time, i.e. the period between launching of the transmitted signal and the receiving of the echo can be used to generate a so called A-image (see Bergmann, L., "Der Ultraschall", S. Hirzel-Verlag, Stuttgart 1954; Matauschek, J., "Einführung in die Ultraschalltechnik", VEB-Verlag Technik, Berlin 1961, and Krautkrämer, J. and Krautkramer, H., "Werkstoffprüfung mit Ultraschall", Springer-Verlag 1975.) This transit time is also directly proportional to the thickness of the tissue which can be calculated directly therefrom, if, in fact, the speed of acoustic waves in the tissue is known.

Aside from the echos being produced on boundaries or impedance changes, the tissue itself absorbs part of the ultrasonic energy, whereby, however, the absorption depends on the frequency of the sonic or ultrasonic signal. Nevertheless, similarly structured boundaries and layers but being located deeper in the tissue will produce only weak echos on account of the aborption of the incident as well as of the reflected signal. In order to compensate for this reduction in amplitude, one has introduced a technique which can be described as transit time dependent amplification or depth compensation. Since a long transit time goes hand in hand with a weak echo signal, one will increase the amplifier gain the longer the delay of the expected or actually appearing echo, metered from the launching time of the test pulse.

This depth compensation has been provided for empirically. One simply selected the proper amplification on the basis of empirical tests and trial and error methods, i.e. on a highly subjective basis. As far as we know, no tissue-dummy or reference standard has yet been suggested by means of which one can objectively calibrate and adjust ultrasonic testing equipment in order to compensate the declining amplitude of echos being returned from deeper boundaries of and in the cell tissue.

DESCRIPTION OF THE INVENTION

It is an object of the present invention to provide a means which permits depth compensation of pulse echo operated ultrasonic equipment used for medical diagnostics.

In accordance with the preferred embodiment of the invention, it is suggested to provide for a new stratified calibration dummy which produces a sequence of echo pulses whose peaks represent the expected depth dependency of echo signals, so that the ultrasonic diagnostic equipment and particularly the receiver circuit thereof, exhibiting time dependent variable gain, can be calibrated, whereupon all of the echo pulses from the reference standard will exhibit equal amplitude. This then represents the correct calibration.

The stratified standard or dummy to be constructed should have multiple, parallel, equidistantly spaced, or near equidistantly spaced, impedance boundaries, wherein the impedance changes to the same degree as can be expected in human cell tissue. The impedance values themselves should be well in the range, as a sort of average, of impedance values as they occur in physiological substances. Speed of ultrasound and absorption of the standard substances must likewise be similar to the corresponding parameters of human cell tissue.

The dummy or standard is constructed from several, stacked containers, separated by thin foils and alternately filled with two substances (liquids) which are different and, exhibit to some extent, different propagation characteristics for acoustic waves (speed, acoustic impedance, absorption) but the difference is not a significant one, and these characteristics of both substances are similar to the corresponding characteristics of human or animal cell tissue. As a consequence, an ultrasonic transmitter pulse launched, e.g. straight down into the stack, produces many echos, and their amplitudes decline with increasing transit time in such a manner that a time dependent gain can be made to reproduce these pulses at constant amplitudes. One will use different oils as calibration substances, exhibiting about 10% difference in acoustic impedance. Each boundary produces the same percentage reflection because the impedance jump is the same.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a cross-section of a calibration and adjusting dummy or reference standard in accordance with the preferred embodiment of the present invention.

According to the detailed description of the drawings, FIG. 1 shows a stack of flat containers 9 and 10 which alternate in the stack. The stack, further, has an upper or top container 8 and a bottom plate 11 closing the lowest container 10. The various containers are actually quite similarly constructed and are separated from each other by thin Teflon or polyamide foils, each being about 0.1 mm thick or thinner.

Take the uppermost foil 1, it is fastened to the container 8 by means of a clamping ring 2 and screws 3. The clamping ring also tensions the foil taut into a flat, planar configuration. Container body 8 is sealed against the clamping ring by an O-ring 4. The foil 1 on top of container 8 establishes also the entrance discontinuity into the reference standard.

The various containers are stacked and their interior is separated by such foils 1, all of which extend parallel to each other. Each foil is in particular fastened to the respective container underneath and by means of such a clamping ring as well as by screws. The containers themselves are, in fact, bottomless, except the container 10 being closed by bottom plate 11. As to the others, the top foil of the respective container underneath constitutes the bottom of any and all of the containers 8 and 9 and the other containers 10.

The containers themselves or, better, the annular frames as stacked, are sealed against each other by means of O-rings 6. Suitably arranged bolts 13 tie the entire assembly together. The various chambers may have circular configuration and the bolts are distributed regularly and on a circle. Each container has two vertical ducts. One duct, denoted by numeral 18, extends axially from top to bottom of the container frame, but there is also a transverse duct portion leading laterally from the outside to the interior of the respective container chamber. A sealing nut 12 closes the lateral duct. Additionally, each container has another axial duct 19 without such lateral portion.

The containers are now stacked so that the ducts 18 with cross-duct of container 8, and ducts 18 of all containers 9, are aligned among each other and are aligned with the ducts 19 (without cross-ducts) of containers 10. The individual ducts are sealed by means of O-rings circumscribing one end of each such duct 18, 19, the sealing being effective as against the joint between respective two stacked container frames. As to other ducts, ducts 18 of containers 10 are aligned with ducts 19 of containers 8 and 9. As a consequence, two separate, rather long ducts traversing all of the container frames, are established, but they are kept separate and communicate separately with two different sets of container interiors.

The several aligned ducts are closed by means of venting screws 5 which permit pressure equalization of the interior of the chambers with the outside (atmospheric pressure). This is desirable to prevent the foils from deflecting out of a planar configuration.

The containers 8 and 9 are now filled with a liquid 14 and containers 10 are filled with a liquid 15. Liquid 14 is, for example, castor oil, having a density $\rho = 0.95$ g/cm$^3$, a speed of sound $c = 1520$ m/sec. resulting in an acoustic impedance $\rho \cdot c = 1.46 \cdot 10^5$ g/cm$^2$sec. The coefficient of absorption for ultrasonic pressure waves is 0.6 cm$^{-1}$. Liquid 15 is, for example, Shell Talpa oil 969, having a density of 0.883 g/cm$^3$; a speed of sound 1480 m/sec, resulting in an acoustic impedance $\rho \cdot c$ of $1.31 \cdot 10^5$ g/cm$^2$sec, further having a coefficient of absorption for such waves of 0.5 cm$^{-1}$. The various data have validity for a temperature of about 20° to 24° C and a frequency of 4 MHz.

The two sets of containers have different heights $r = 19.44$ mm and $t = 18.8$ mm, which values are selected to that they correspond to tissue of particular thickness. The absorption of the two liquids is almost the same and corresponds to the absorption of regular muscle tissue.

In practice, an ultrasonic transmitter/receiver type transducer 16 is disposed on top foil 1 and issues calibration pulses straight down. The reflected echos are received and they are regularly spaced corresponding to a regular difference in transit time. These echo peaks outline a curve which represents the absorption increase with transit time, upon which is superimposed the attenuation resulting from the fact that the incident beam from which a portion is reflected back, has been weakened by several previous reflections. However, the loss of the incident beam due to such multiple reflection on several parallel boundaries, can, in effect, be neglected, because the reflection coefficient during transit from #14 to #15 is about 0.29%, i.e. the boundary passes 99.85% of the incident beam, which is a deviation of no consequence. The ultrasonic receiver circuit is now adjusted as to its time dependent gain, so that all echo peaks have (at least on the average) equal amplitude.

The invention is not limited to the embodiments described above but all changes and modifications thereof not constituting departures from the spirit and scope of the invention are intended to be included.

We claim:

1. Calibration dummy for simulating cell tissue, comprising:

a stack of containers, separated from each other by thin foils and defining a path for transmission of ultrasonic waves, the containers being alternately filled with two different liquids, differing in their ultrasonic impedance, but both having acoustic speed, absorption and acoustic impedance values similar to the respective values for different human or animal cell tissue.

2. Calibration dummy as in claim 1, wherein containers holding the same kind of liquid are fluid conductively interconnected.

3. Calibration dummy as in claim 1, wherein the liquids are different oils.

4. Calibration dummy as in claim 1, one oil being castor oil, the other one a mineral oil.

* * * * *